Feb. 26, 1957 E. S. BOERNER Plant Pat. 1,570
ROSE PLANT
Filed May 16, 1956
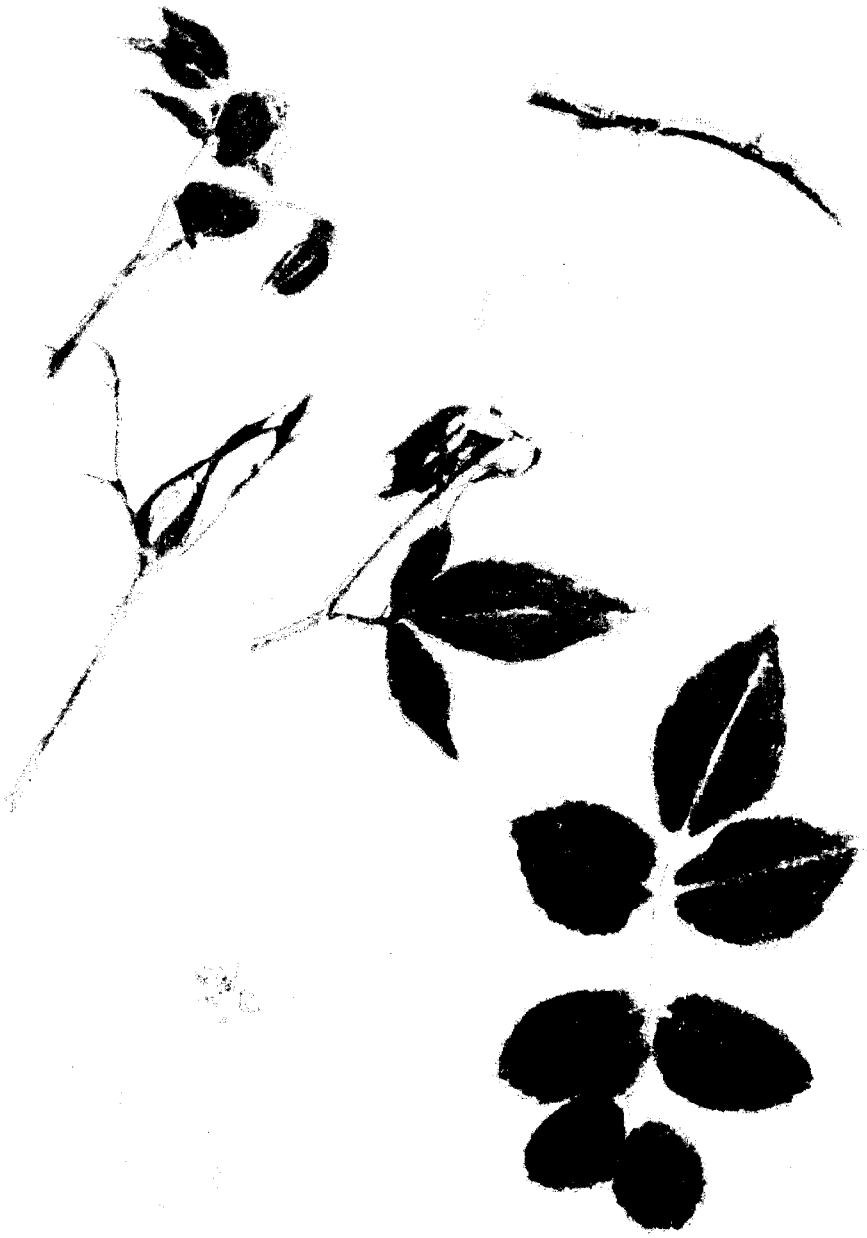
Inventor.
E. S. Boerner
By: Robbins & Robbins
Attorneys.

United States Patent Office

Plant Pat. 1,570

Patented Feb. 26, 1957

1,570

ROSE PLANT

Eugene S. Boerner, Newark, N. Y., assignor to Jackson & Perkins Company, Newark, N. Y., a corporation of New York Application May 16, 1956, Serial No. 585,371

1 Claim. (Cl. 47—61)

The present invention relates to a new and distinct variety of rose plant of the large-flowered polyantha class, which was originated by me by crossing the variety "Goldilocks" (Plant Patent No. 672) with the variety "Garnette" (unpatented).

The primary objective of this breeding was to produce a new rose variety of the floribunda type which bears longer-lasting flowers that are suitable for use as cut flowers. This objective was fully achieved, along with other differentiating characteristics, as evidenced by the following features which are outstanding in the new variety:

(1) The improved long-lasting quality of the floribunda type flowers which have keeping qualities equal to that of the parent variety "Garnette";

(2) The decided branching of the sepals, with a "hood" above the bud;

(3) The distinctive Thulite Pink, lightly overcast with Deep Rose Pink, general color tonality of the flowers, which is a new color in the cut flower field; and (4) The distinctive Vandyke Red coloring in the new foliage, which is unusual in a rose of this color.

The foregoing characteristics and distinctions definitely differentiate my new variety from its parents, as well as from all other varieties of its class of which I am aware.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and the flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—"Goldilocks."

*Pollen parent.*—"Garnette."

Classification:

*Botanic.*—Large-flowered polyantha.

*Commercial.*—Floribunda.

*Flower*

(Observations made from specimens grown in a greenhouse at Newark, New York, in the early part of the month of April, and in the early morning.)

Blooming habit: Recurrent—continuous.

Bud:

*Size.*—Medium.

*Form.*—Ovoid; is not affected by wet or hot weather.

*Color.*—When sepals first divide—Begonia Rose, Plate 1. When petals begin to unfurl—Eosine Pink, Plate 1. When half-blown: inside of petals—Deep Rose Pink, Plate 12, lightly overcast with Thulite Pink, Plate 26; reverse of petals—Eosine Pink, Plate 1, lightly overcast with Spinel Pink, Plate 26.

*Sepals.*—Branched, with "hood" above bud; curl back when petals begin to unfurl. Color: inside—Absinthe Green, Plate 31; outside—Deep Dull Yellow-Green, Plate 32.

*Calyx.*—Color—Deep Dull Yellow-Green, Plate 32. Shape—funnel. Size—small. Aspect—smooth. Odor when rubbed—none.

*Peduncle.*—Length — medium. Aspect — rough. Strength—stiff; slender. Color—Cerro Green, Plate 5.

*Opening.*—Opens up well; is not affected by adverse weather conditions.

Bloom:

*Size.*—Medium. Average size when fully expanded—from 2½ to 3 inches.

*Borne.*—Several together and in clusters.

*Stems.*—Medium length; normal strength.

*Form (when first opened).*—From cupped to open. Permanence—flattens.

*Petalage.*—Very double (many petals and stamens hidden). Number of petals under normal conditions—from 35 to 40.

*Color.*—Center of flower—Deep Rose Pink, Plate 12, lightly overcast with Thulite Pink, Plate 26. Outer petals—Thulite Pink, Plate 26. Base of petals (aiglet)—Martius Yellow, Plate 4. Inside of petals—Thulite Pink, Plate 26, lightly overcast with Deep Rose Pink, Plate 12. Reverse of petals—Cameo Pink, Plate 26, lightly overcast with Rose Pink, Plate 12. General tonality from a distance—Deep Rose Pink, Plate 12, lightly overcast with Thulite Pink, Plate 26.

*Discoloration.*—General tonality at end of first day—Deep Rose Pink, Plate 12, lightly overcast with Thulite Pink, Plate 26. Second day—Thulite Pink, Plate 26, lightly overcast with Deep Rose Pink, Plate 12. Third day—Thulite Pink, Plate 26, lightly overcast with Rose Pink, Plate 12.

Petals:

*Texture.*—Thick; leathery; is not affected by wet or hot weather.

*Appearance.*—Inside—satiny. Outside—shiny.

*Form.*—Oval.

*Arrangement.*—Imbricated (regularly arranged shingle-like).

*Petaloids in center.*—Few; small.

*Persistence.*—Drop off cleanly.

*Fragrance.*—Moderate. Nature—"Old Rose perfume" (Centifolia).

*Lasting quality.*—On the plant—very long. As cut flower—very long.

*Genital organs*

Stamens, anthers: Medium size; few, regularly arranged around styles. Color—Orange Buff, Plate 3.

Stamens, filaments (threads): Medium length. Color—Martius Yellow, Plate 4.

Pollen: Color—Maise Yellow, Plate 4.

Styles: Columnar; uneven length; short; thin.

Stigmas: Color—Light Green Yellow, Plate 5.

Ovaries: All enclosed in calyx.

Hips: None.

Seeds: None.

*Plant*

Form: Bush.

Growth: Vigorous; upright; bushy.

Foliage: Compound of 5 to 7 leaflets.

*Size.*—Medium.

*Quantity.*—Normal.

*Color.*—New foliage: upper side—Yellowish Oil Green, Plate 5, overcast with Vandyke Red, Plate 13; under side—"Garnet Brown," Plate 1, lightly overcast with Olive Green, Plate 4. Old foliage: upper side—Varley's Green, Plate 18; under side—Light Cress Green, Plate 31.

*Shape.*—Oval pointed.

*Texture.*—Upper side—leathery; glossy. Under side—smooth.

*Ribs and veins.*—Ordinary.

*Edge.*—Serrated (saw-toothed).

*Serration.*—Single; small.

*Leaf stem.*—Color—Garnet Brown, Plate 31. Under side—rough.

*Stipules.*—Medium length; bearded.

Wood:

*New wood.*—Color—Parrot Green, Plate 6. Bark—smooth.

*Old wood.*—Color—Spinach Green, Plate 5. Bark—smooth.

Thorns:

*Thorns.*—Quantity: on main stalks from base—ordinary; on laterals from stalk—ordinary. Form—medium length; straight; with narrow base. Color (when young)—Carmine, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by the long-lasting quality of its flowers, the decided branching of the sepals, with a "hood" above the bud, the distinctive Thulite Pink, lightly overcast with Deep Rose Pink, general color tonality of its flowers, and the distinctive Vandyke Red coloring in its new foliage.

No references cited.